(12) United States Patent
Karnes et al.

(10) Patent No.: US 9,603,608 B2
(45) Date of Patent: *Mar. 28, 2017

(54) METHOD FOR FORMING NON-CIRCULAR CARTILAGE GRAFTS

(71) Applicant: Arthrex, Inc., Naples, FL (US)

(72) Inventors: G. Joshua Karnes, Naples, FL (US); John M. Konicek, Naples, FL (US); David O. Shepard, Naples, FL (US); Brandon L. Roller, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/964,142

(22) Filed: Dec. 9, 2015

(65) Prior Publication Data

US 2016/0081700 A1    Mar. 24, 2016

Related U.S. Application Data

(63) Continuation of application No. 14/180,949, filed on Feb. 14, 2014, now Pat. No. 9,216,022.

(Continued)

(51) Int. Cl.
| | |
|---|---|
| *A61B 17/16* | (2006.01) |
| *A61B 17/15* | (2006.01) |
| *A61B 17/17* | (2006.01) |
| *A61F 2/28* | (2006.01) |
| *A61F 2/46* | (2006.01) |
| *A61B 17/92* | (2006.01) |
| *A61F 2/30* | (2006.01) |

(Continued)

(52) U.S. Cl.
CPC ........ *A61B 17/1635* (2013.01); *A61B 17/155* (2013.01); *A61B 17/1604* (2013.01); *A61B 17/1606* (2013.01); *A61B 17/1675* (2013.01); *A61B 17/1764* (2013.01); *A61B 17/92* (2013.01); *A61F 2/28* (2013.01); *A61F 2/4644* (2013.01); *A61B 2017/0046* (2013.01); *A61B 2090/062* (2016.02); *A61F 2002/2839* (2013.01); *A61F 2002/30764* (2013.01); *A61F 2002/4645* (2013.01); *A61F 2002/4649* (2013.01)

(58) Field of Classification Search
CPC ................................................ A61B 17/1635
See application file for complete search history.

(56) References Cited

U.S. PATENT DOCUMENTS

| | | |
|---|---|---|
| 5,919,196 A | 7/1999 | Bobic et al. |
| 6,488,033 B1 | 12/2002 | Cerundolo |

(Continued)

*Primary Examiner* — Andrew Yang
(74) *Attorney, Agent, or Firm* — McDonnell Boehnen Hulbert & Berghoff LLP

(57) ABSTRACT

A technique for knee replacement surgery that allow for the removal of an oval oblong-shaped allograft bone and cartilage plug from a donor distal femur. The technique uses instruments including (i) sizing guides to match the recipient's femoral size and curvature to that of a donor femur (the sizing guides also acting as a wide pin placement template for the donor distal femur); (ii) osteotomes that cut the curved and straight portions of the implant shape (these may be disposable or reusable); and (iii) templates that fit over the guide pins and have openings to allow the osteotomes to cut the donor femur plug to the correct size, shape and depth. The instruments allow for a non-circular shape to be extracted from a donor femur for use in a bone-saving osteoarthritis distal femur resurfacing procedure.

14 Claims, 23 Drawing Sheets

Related U.S. Application Data

(60) Provisional application No. 61/765,249, filed on Feb. 15, 2013.

(51) Int. Cl.
 *A61B 17/00* (2006.01)
 *A61B 90/00* (2016.01)

(56) References Cited

U.S. PATENT DOCUMENTS

| | | |
|---|---|---|
| 6,591,581 B2 | 7/2003 | Schmieding |
| 6,592,588 B1 | 7/2003 | Bobic et al. |
| 7,160,305 B2 | 1/2007 | Schmieding |
| 7,264,634 B2 | 9/2007 | Schmieding |
| 7,959,636 B2 | 6/2011 | Schmieding |
| 8,012,172 B2 | 9/2011 | Grafton et al. |
| 2006/0247790 A1 | 11/2006 | McKay |

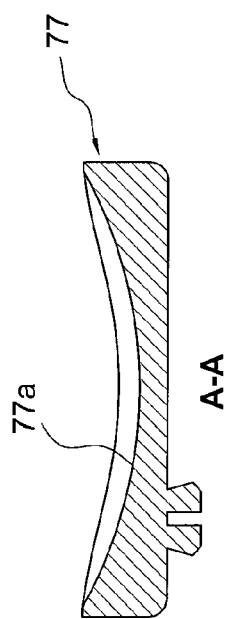
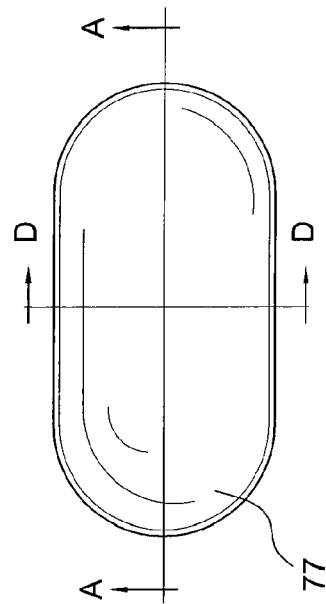
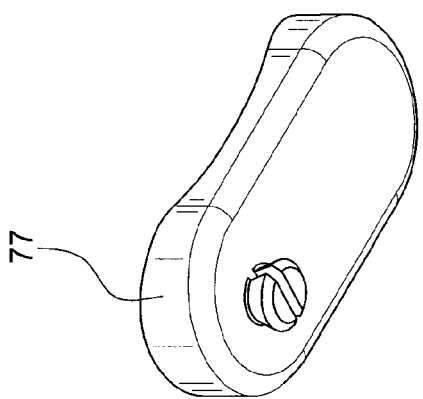

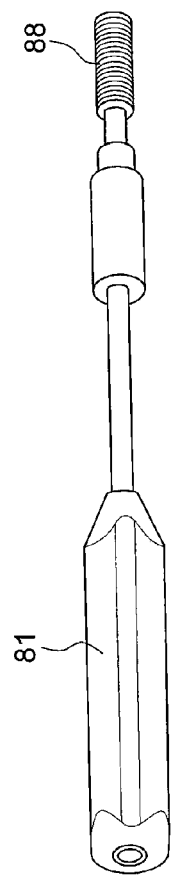
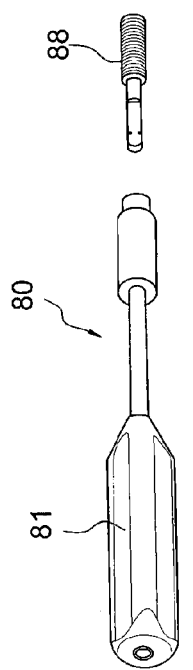
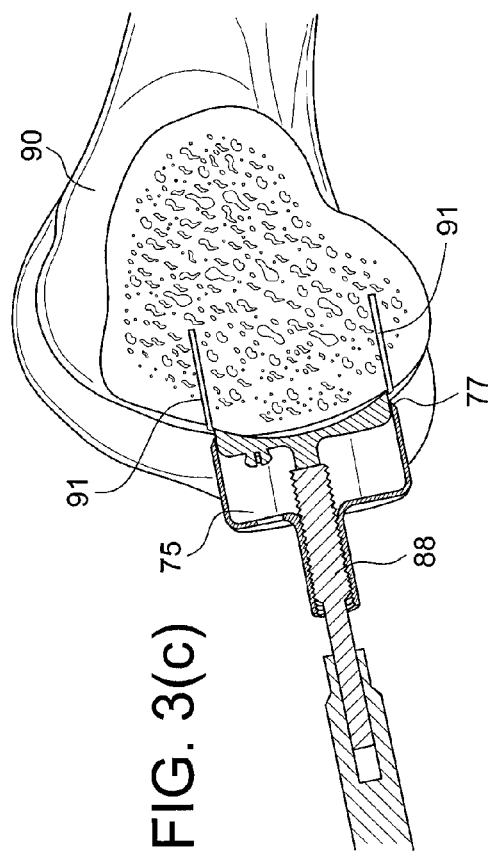
FIG. 3(a)
FIG. 3(b)
FIG. 3(c)

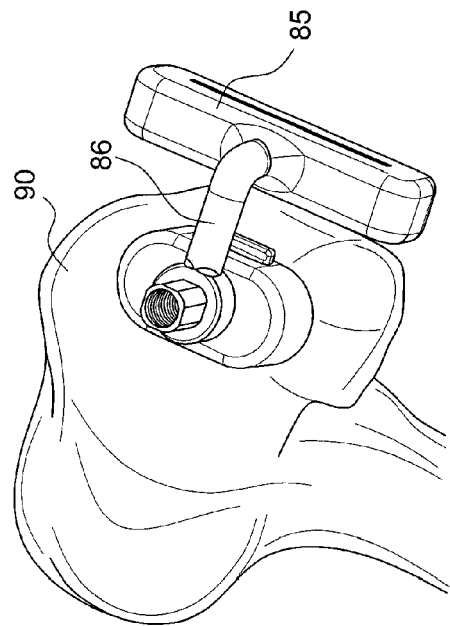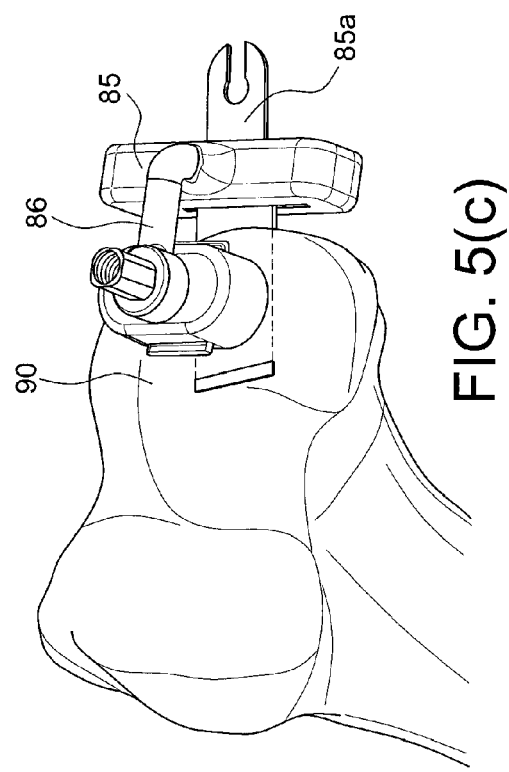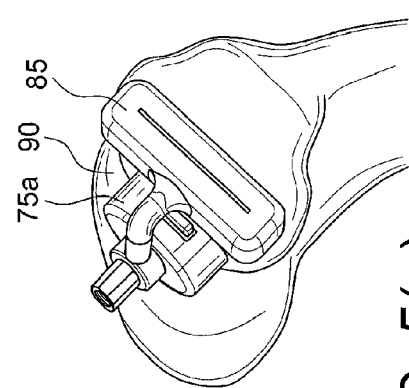
FIG. 5(a)
FIG. 5(b)
FIG. 5(c)

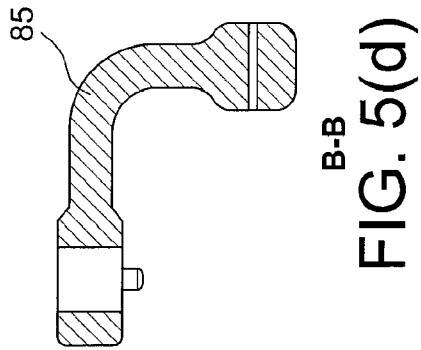
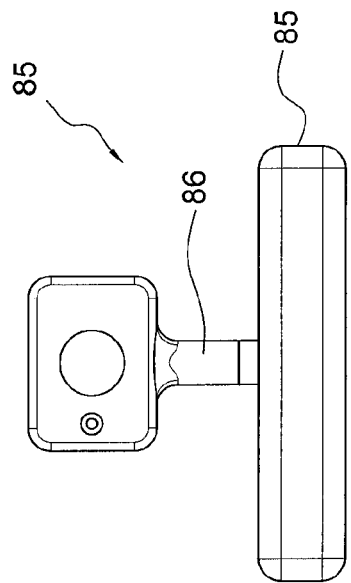
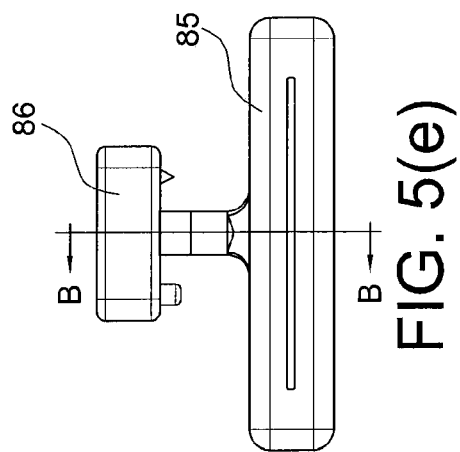

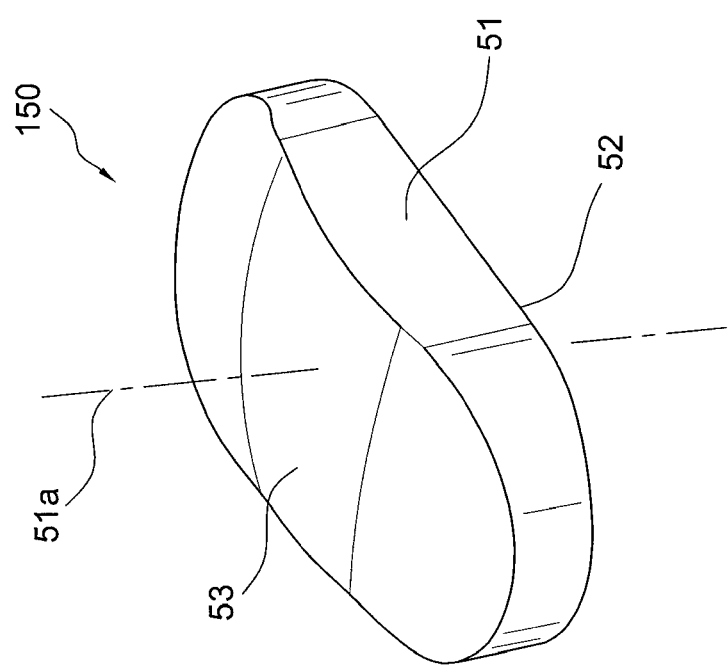

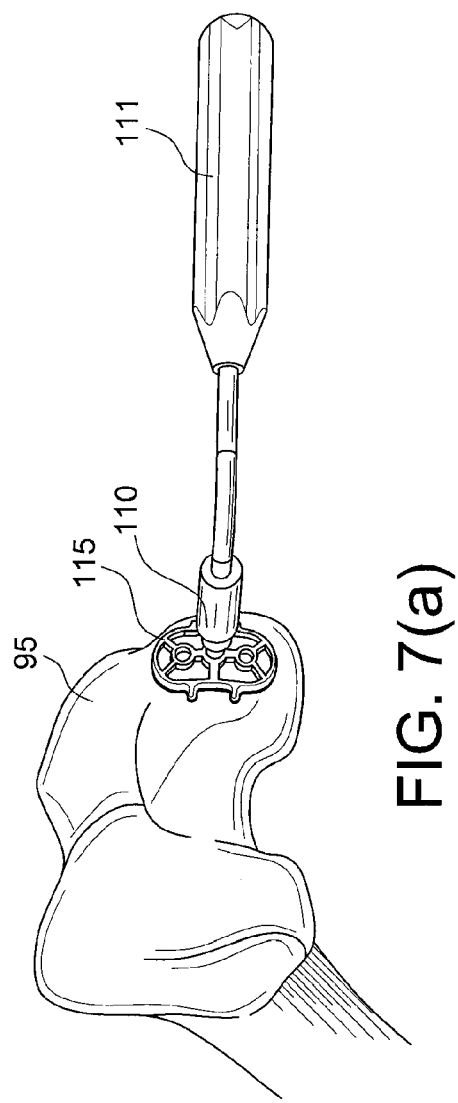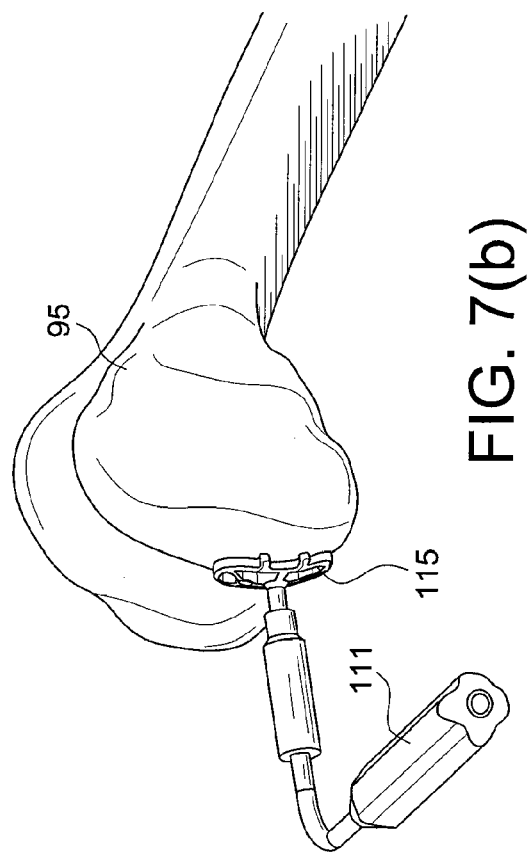
FIG. 7(a)
FIG. 7(b)

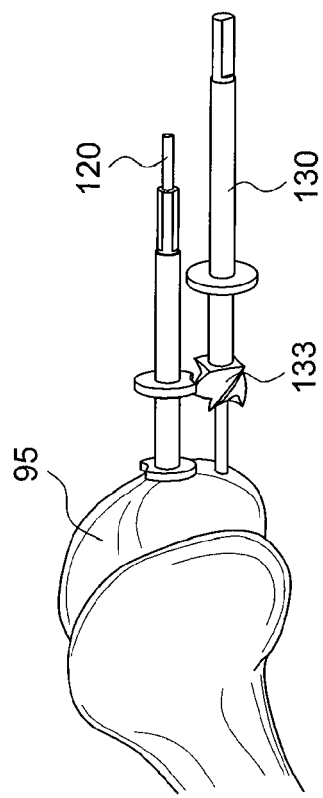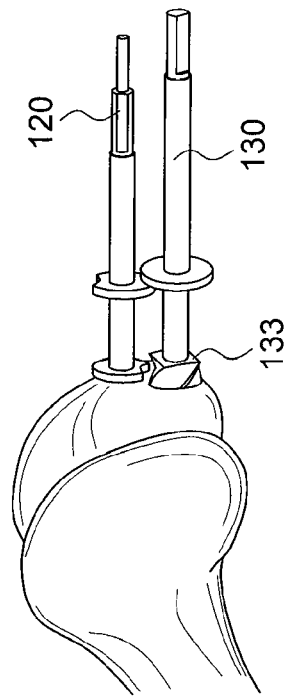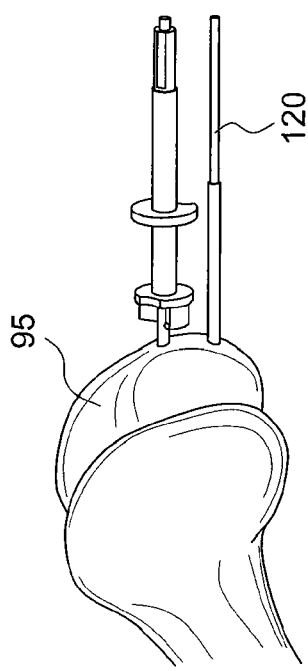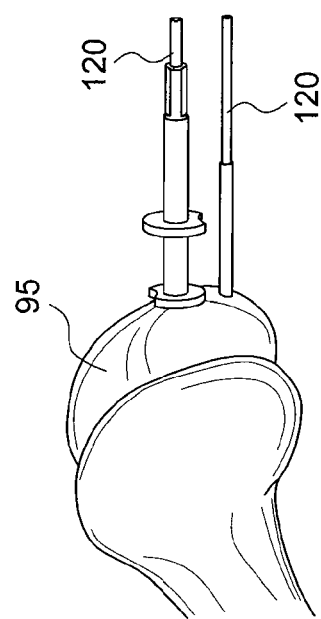

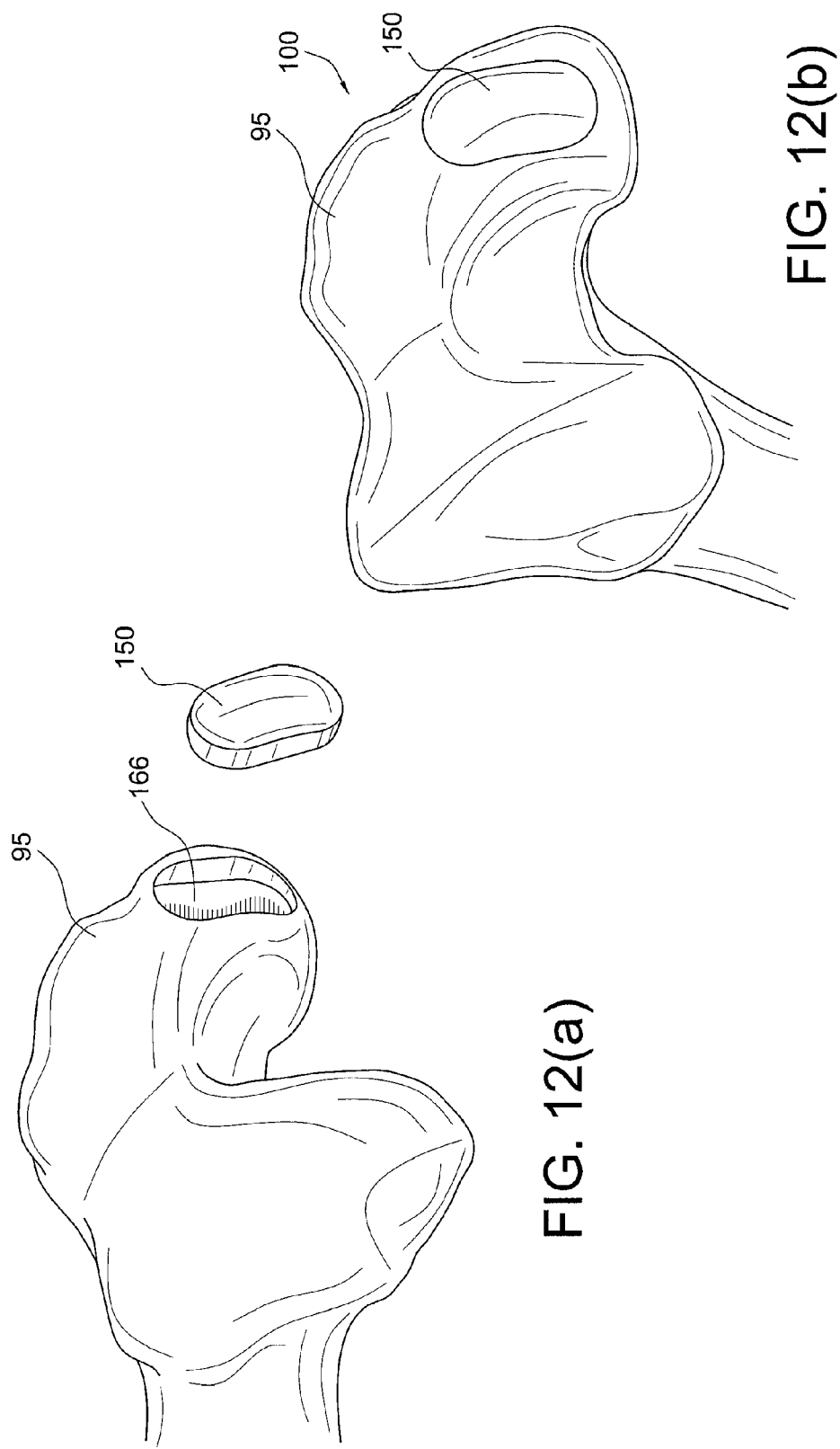

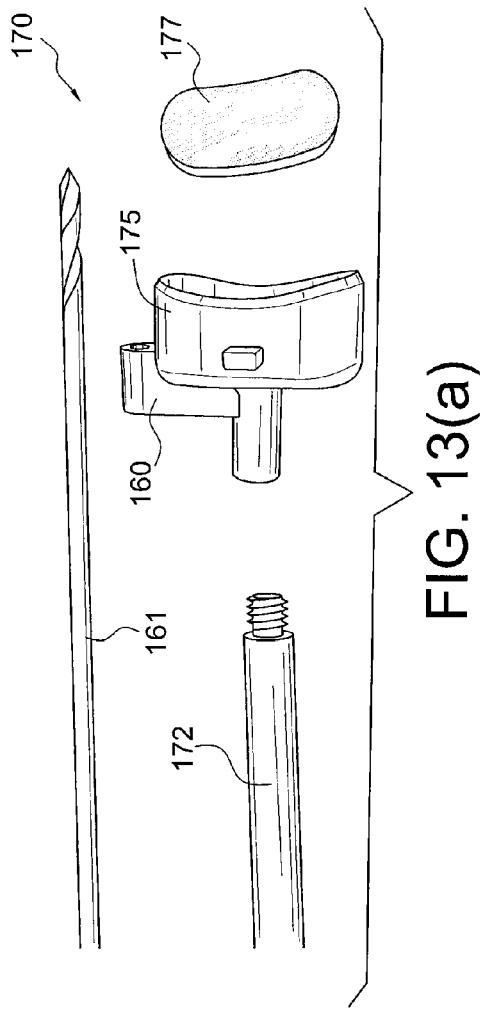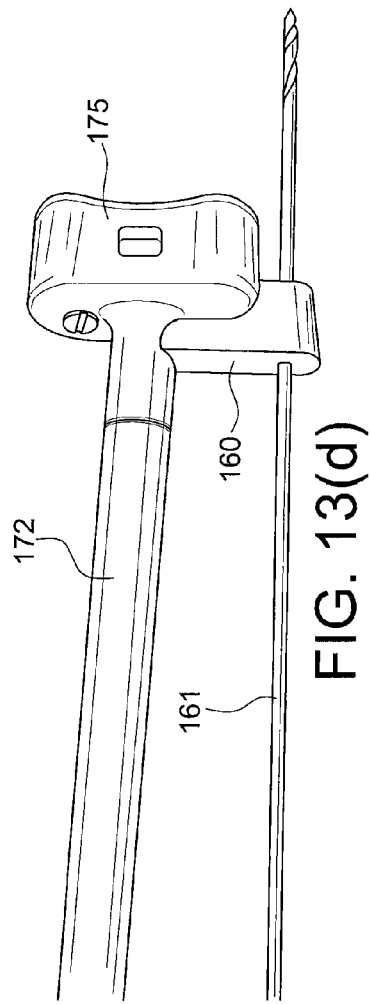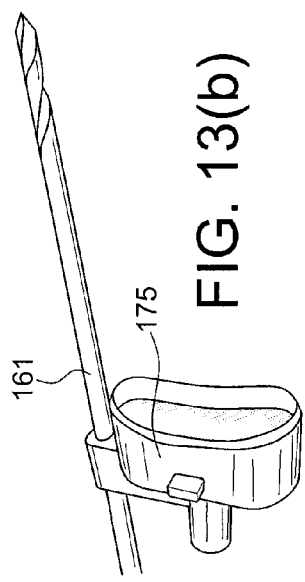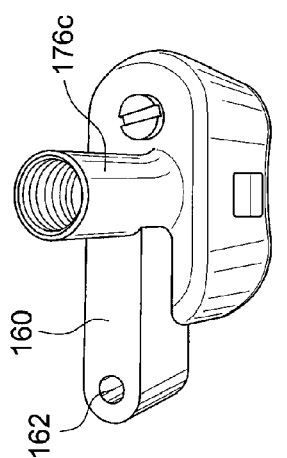
FIG. 13(a)
FIG. 13(b)
FIG. 13(c)
FIG. 13(d)

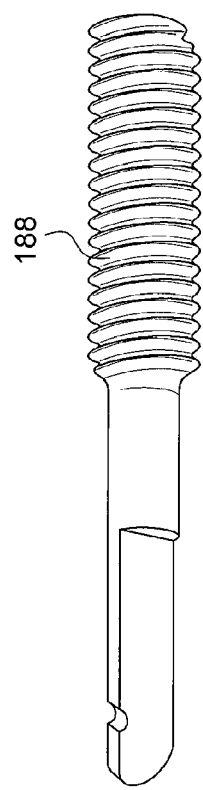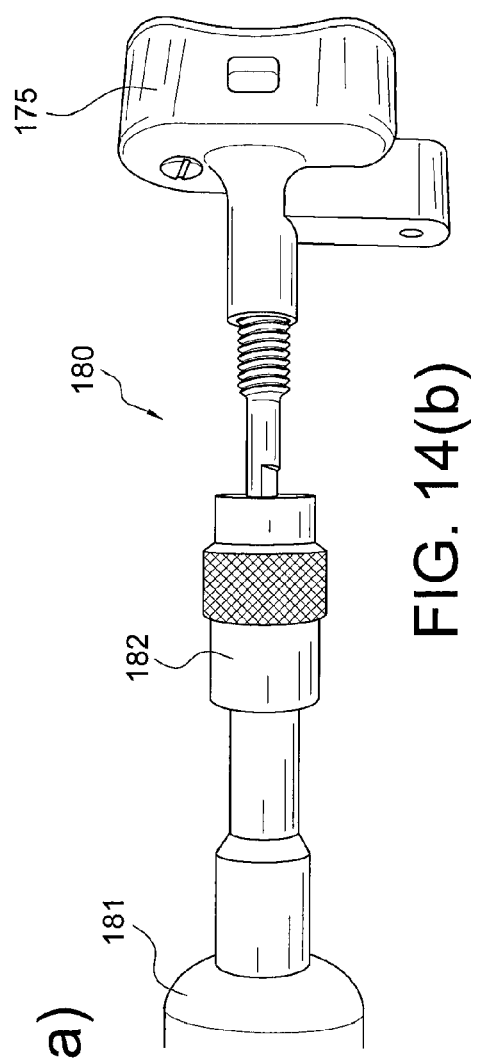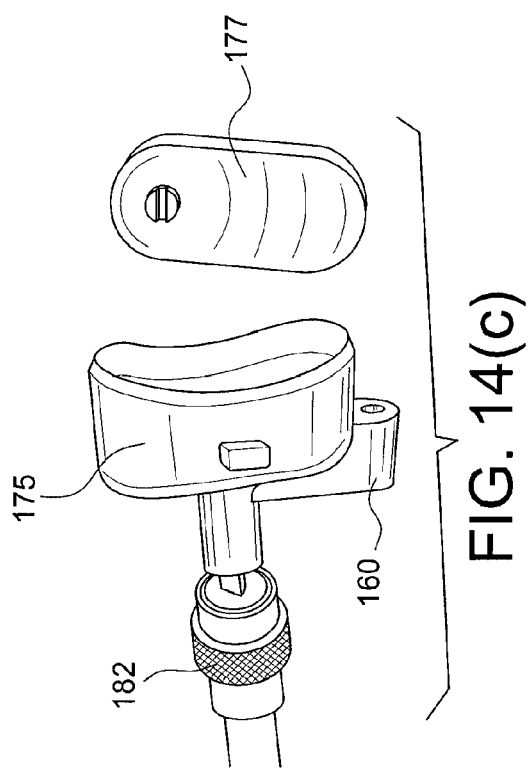

METHOD FOR FORMING NON-CIRCULAR CARTILAGE GRAFTS

CROSS-REFERENCE TO RELATED APPLICATIONS

This application is a continuation of U.S. application Ser. No. 14/180,949, filed Feb. 14, 2014, (now U.S. Pat. No. 9,216,022), which claims the benefit of U.S. Provisional Application No. 61/765,249, filed Feb. 15, 2013, the disclosures of which are incorporated by reference in their entirety herein.

FIELD OF THE INVENTION

The present invention relates to the field of arthroscopic surgery and, more particularly, to methods of reconstructive knee surgery.

BACKGROUND OF THE INVENTION

Knee replacement surgery, also called knee arthroplasty, is routinely considered for the treatment of osteoarthritis of the knee joint. Partial knee replacement surgery has generated significant interest because it entails a smaller incision and faster recovery than traditional total joint replacement surgery.

When partial knee replacement is performed, the bone and cartilage on the end of the femur and top of the tibia are removed. This is performed using precise instruments to create exact surfaces to accommodate an implant. A knee replacement implant made of various biocompatible materials such as metal or plastic is then placed to function as a new knee joint.

The typical arthritic cartilage damage pattern is oval or oblong in shape; however, the current techniques only allow for a circular allograft bone plug implant, or for a metal or plastic oval or oblong implant. Thus, the circular shape of the allograft implant does not correspond to the oblong or oval shape of the defect.

There is a need for a non-circular shape implant to be extracted from a donor femur for use in a bone-saving osteoarthritis distal femur resurfacing procedure. Also needed are instruments and techniques that allow matching of the recipient's femoral size and curvature to that of a donor femur (and to cut the donor femur cartilage plug to the correct size, shape and depth).

SUMMARY OF THE INVENTION

The present invention provides techniques and instruments for knee replacement surgery that allow for the removal of an oval oblong-shaped allograft bone and cartilage plug from a donor distal femur.

The invention provides (i) sizing guides to match the recipient's femoral size and curvature to that of a donor femur (the sizing guides also acting as a wide pin placement template for the donor distal femur); (ii) osteotomes that cut the curved and straight portions of the implant shape (these may be disposable or reusable); and (iii) templates that fit over the guide pins and have openings to allow the osteotomes to cut the donor femur plug to the correct size, shape and depth. These instruments allow for a non-circular shape to be extracted from a donor femur for use in a bone-saving osteoarthritis distal femur resurfacing procedure.

The present invention also provides methods of forming non-circular cartilage grafts for the treatment of osteoarthritis of a knee joint by inter alia (i) using a 3D template to define the size and position of the harvest site (on the template, there are at least two holes for placing alignment pins for subsequent steps—holes are outside the harvest site); (ii) inserting a guide over the drill pins placed in step (i) to cut or drill, for example; and (iii) placing a second guide to create more cuts if necessary.

Although the present invention is described below in connection with a knee procedure, the invention can also advantageously be used for similar procedures in joints other than the knee joint.

Other features and advantages of the present invention will become apparent from the following description of the invention which refers to the accompanying drawings.

BRIEF DESCRIPTION OF THE DRAWINGS

FIGS. 1(h)-1(k) illustrate various views of the cutter insert of the system of FIG. 1(a).

FIG. 3(a) illustrates an expanded view of an exemplary distractor system used to remove the cutter and insert of the system of the present invention.

FIG. 3(b) illustrates another view of the exemplary distractor system of FIG. 3(a) (in the assembled state).

FIG. 3(c) illustrates how the cutter is distracted from the femur with the distractor system of FIG. 3(b).

FIGS. 4(c)-4(h) illustrate details of the oblong depth guide of the system of FIG. 4(a).

FIGS. 5(a) and 5(b) illustrate depth cutting (donor side) with the oblong depth guide system of FIG. 4(b) and with an exemplary sagittal saw guide of the present invention.

FIG. 5(c) illustrates depth cutting (donor side) with the oblong depth guide system and exemplary sagittal saw guide of FIG. 5(b) and with a saw blade.

FIGS. 5(d)-5(f) illustrate details of the sagittal saw guide of FIG. 5(a).

FIG. 6 illustrates a donor implant of the present invention, formed with the instrumentations and by the steps of FIGS. 1(a)-5(f).

FIGS. 7(a) and 7(b) illustrate various views of an exemplary recipient pin guide of the present invention (including a handle and a recipient guide) used to match the curvature of the recipient femur (recipient side), and according to an embodiment of the present invention.

FIGS. 9(a) and 9(b) illustrate drilling of the ends of the oblong shape recipient hole with the two drills (anterior drills).

FIGS. 10(a) and 10(b) illustrate drilling of the ends of the oblong shape recipient hole with the two drills (posterior drills).

FIG. 12(a) illustrates an exemplary donor implant in the proximity of a recipient femur with a recipient site formed according to the present invention.

FIG. 12(b) illustrates the complete final repair formed by pressing the exemplary donor implant of FIG. 6 into the recipient oblong hole of FIG. 12(a).

FIG. 13(a) illustrates an expanded view of an oblong cutter system and instrumentation (donor side) according to yet another exemplary embodiment of the present invention.

FIG. 13(b) illustrates a perspective view of the oblong cutter system of FIG. 13(a) (in the assembled state, i.e., with a cutter, guide pin, impactor (oblong cutter) and cutter insert).

FIG. 13(c) illustrates an enlarged view of the cutter of the oblong cutter system of FIG. 13(b).

FIG. 13(d) illustrates a perspective view of the oblong cutter system of FIG. 13(a) (in the assembled state).

FIG. 14(a) illustrates an enlarged view of an exemplary distractor used to remove the cutter and insert of the system of the present invention.

FIG. 14(b) illustrates the distractor of FIG. 14(a) used with a handle to remove the cutter insert from the cutter.

FIG. 14(c) illustrates the exemplary distractor system of FIG. 14(b) used to remove the cutter and insert of the system of the present invention.

DETAILED DESCRIPTION OF THE INVENTION

Figure 1A:
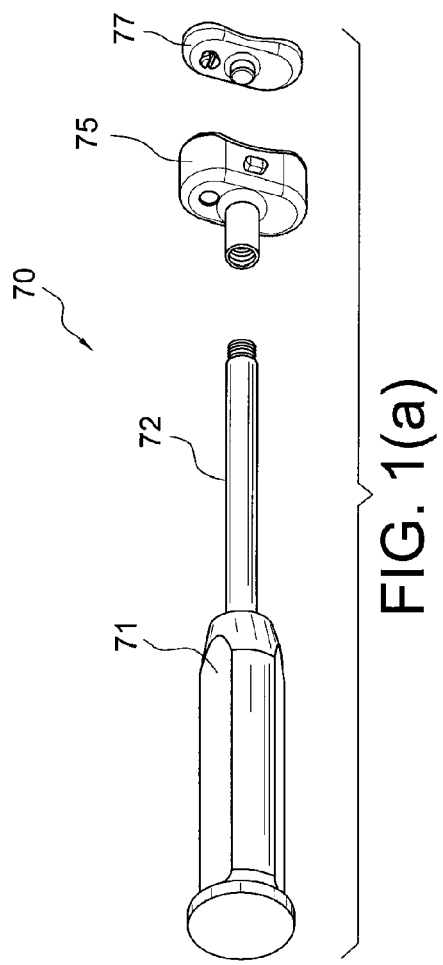
FIG. 1(a) illustrates an expanded view of an oblong cutter system and instrumentation (donor side) according to an exemplary embodiment of the present invention.
Figure 1B:
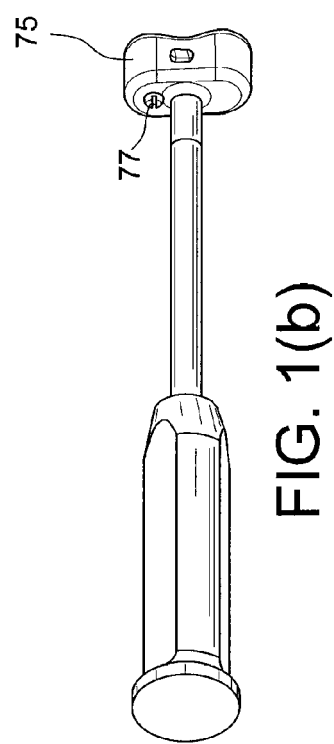
FIG. 1(b) illustrates a perspective view of the oblong cutter system of FIG. 1(a) (in the assembled state).
Figure 1C:
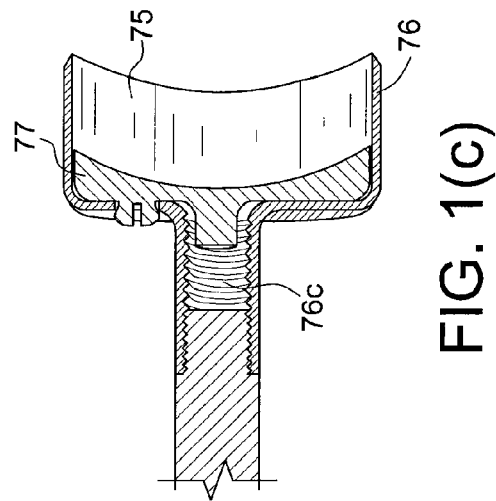
FIG. 1(c) illustrates a cross-sectional enlarged view of the cutter and inserter of the oblong cutter system of FIG. 1(b).
Figure 1E:
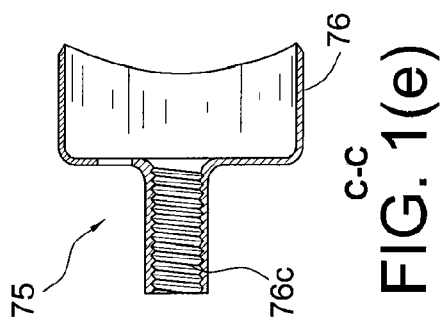
FIGS. 1(d)-1(g) illustrate various views of the oblong cutter of the system of FIG. 1(a).
Figure 1G:
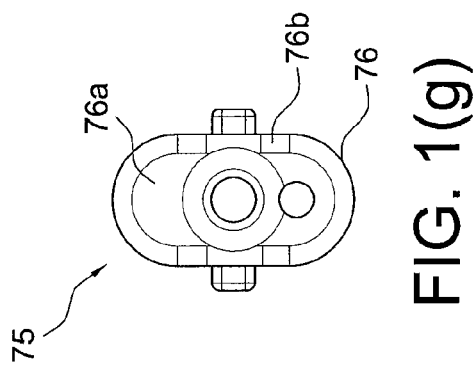
Figure 1D:
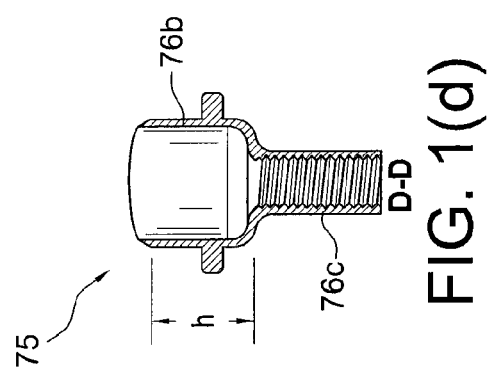
Figure 1F:
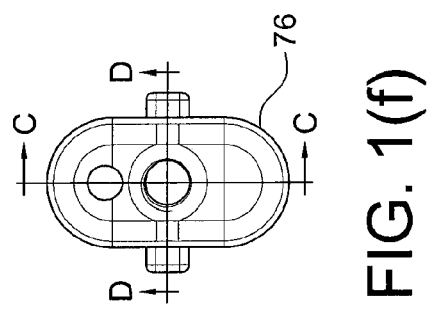

The present invention provides instruments, systems and methods of arthroscopically preparing a femur to accept an oval, oblong shaped implant (a non-circular implant) from a donor femur plug, as part of a method for treating osteoarthritis of a knee joint. The present invention also provides instruments, systems and methods of preparing an oval, oblong shaped implant (an allograft bone and cartilage plug) having a non-circular configuration/shape for treating osteoarthritis of a joint (for example, in an osteoarthritis distal femur resurfacing procedure).

The instruments and systems of the invention include at least one of the following devices: (i) sizing guides to match the recipient's femoral size and curvature to that of a donor femur (the sizing guides also acting as a wide pin placement template for the donor distal femur); (ii) osteotomes that cut the curved and straight portions of the implant shape (these may be disposable or reusable); and (iii) sizing templates that fit over the guide pins and have openings to allow the osteotomes to cut the donor femur plug to the correct size, shape and depth.

The instruments of the present invention allow for a non-circular shape allograft (for example, an oval or oblong shaped allograft bone and cartilage plug) to be extracted from a donor femur for use in a bone-saving osteoarthritis distal femur resurfacing procedure. In an exemplary embodiment, and as detailed below, the fixtures used in the design include: 1) sizing guides to match the recipient's femoral size and curvature to that of a donor femur, and the sizing guides also act as a guide pin placement template for the donor distal femur; 2) osteotomies that cut the curved and straight portions of the implant shape; these may be disposable or reusable; and 3) templates the fit over the guide pins and have openings to allow the osteotomes to cut the donor femur plug to the correct size, shape and depth.

As detailed below, the invention allows for a non-circular shape to be extracted from a donor femur for use in a bone-saving osteoarthritis distal femur resurfacing procedure. The typical arthritic cartilage damage pattern is oval or oblong in shape, and current art only allows for a circular allograft bone plug implant or for a metal or plastic oval or oblong implant. Thus, the invention allows for the combination of the correct implant shape with allograft donor materials. The single-piece, allograft plugs of the present invention consist essentially of cartilage and bone, have a non-circular shape (oval or oblong or combination thereof) and have a height as small as about 5 mm.

Referring now to the drawings, where like elements are designated by like reference numerals, FIGS. 1(a)-18(b) illustrate exemplary surgical instruments, kits and systems of the present invention, for methods of resurfacing a distal femur (for exemplary treatment of osteoarthritis of a knee joint). Exemplary repair 100 is shown in FIG. 12(b), which shows donor implant 150 with a non-circular configuration (shape) of the present invention secured to a femoral recipient site 166 for receiving the donor implant 150.

As detailed below, the donor implant 150 of the present invention is formed by employing specific instrumentation and by a sequence of specific steps (i.e., providing an impactor to impact a cutter assembly with a cutter with guide pin and a cutter insert; providing a distractor to remove the cutter insert from the cutter; and providing a donor depth guide and saw guide assembly with a sagittal saw blade to cut the bone block and release the donor implant).

As detailed below, the femoral recipient site 166 of the present invention may be formed by employing specific instrumentation and by a sequence of specific steps (i.e., providing a sizing device and recipient drill guide with a detachable handle and drill guide pins; providing a broach with an impactor handle and drill bits to form an oblong hole in the recipient femur; providing a recipient cleaning pliers to clean the sides of the oblong hole and match the curvature of the donor implant.

FIGS. 1(*a*)-12(*b*) illustrate instruments and methods employed for allograft reconstruction according to an exemplary embodiment of the present invention. A non-circular shaped implant (an oval oblong shaped and cartilage plug) is extracted from a donor femur 90 for use in a resurfacing procedure by using specialized instruments and procedures. FIGS. 1(*a*)-5(*f*) illustrate the donor side instrumentation for obtaining cut donor implant 150 (curved and oblong) of the present invention (also shown in FIG. 6). FIGS. 7(*a*)-11(*e*) illustrate the recipient side instrumentation for forming a recipient site to secure cut donor implant 150 (curved and oblong) therein.

FIGS. 1(*a*)-1(*c*) illustrate various elements of oblong cutter system 70 (first cutter assembly) and instrumentation of the present invention used on the donor side. Oblong cutter system 70 includes handle 71, impactor 72, oblong cutter 75 and cutter insert 77. FIGS. 1(*d*)-1(*g*) illustrate details and various views of the oblong cutter 75 having a generally oval configuration as seen from the bottom view, for example. Wall 76 has two curved portions 76*a* adjacent and in contact with two straight portions 76*b*. Wall 76 (that has a continuous oval perimeter) has a height "h" (FIG. 1(*d*)). Threaded cylindrical portion 76*c* extends in a direction about parallel to that of the direction of wall 76.

FIGS. 1(*h*)-1(*k*) illustrate details and various views of the cutter insert 77 of cutter system 70. Cutter insert 77 has an outer shape and configuration that resembles the shape and configuration of the inner part of the oblong cutter 75 (i.e., of the region located within the continuous wall 76) so that, when inserted into the cutter 75, the insert 77 tightly engages and fits within the inside of the cutter 75 (i.e., within the inner recess/cannulation of the cutter). Concave region 77*a* is designed to match and contact the femoral cortex, as shown in FIGS. 1(*h*) and 1(*k*), for example. When inserted within the cutter 75, the insert 77 engages the inner region of the wall 76 of the cutter 75, as detailed in FIG. 1(*c*).

Figure 2B:
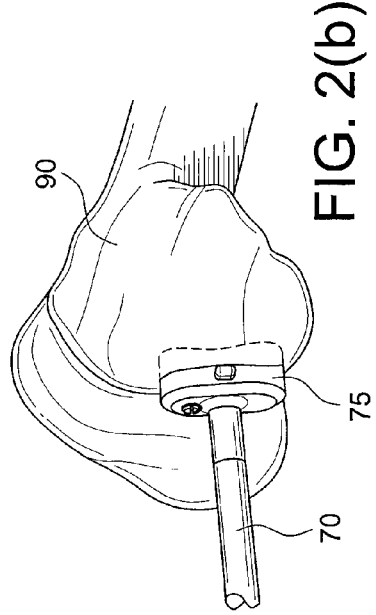
FIGS. 2(a)-2(c) illustrate cutting of the donor femur (donor side) with the cutter of FIG. 1(a).
Figure 2C:
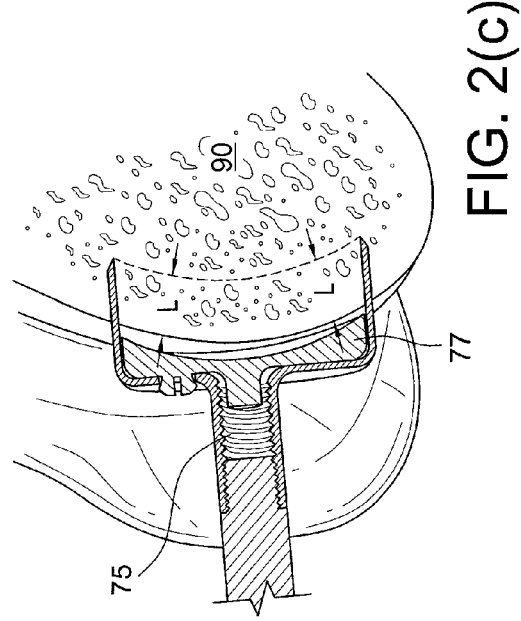
Figure 2A:
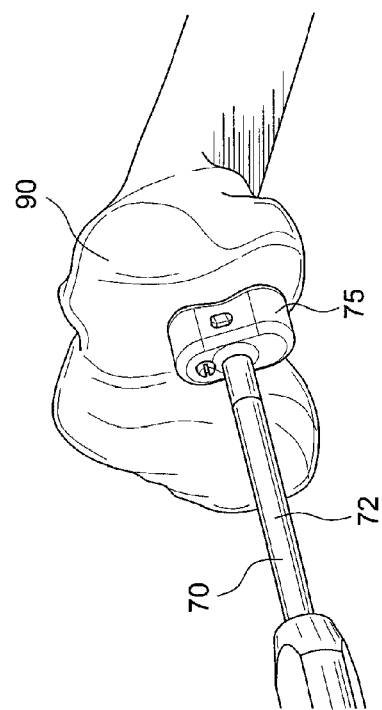

FIGS. 2(*a*)-2(*c*) illustrates cutting of the donor femur 90 (donor side) with the system 70 including oblong cutter 75 (first cutter), insert 77 and impactor 72. The curved cutting edge of cutter 75 is aligned to the surface of the femur 90 (and inserted to hard depth stop) to cut femur 90 a length L (FIG. 2(*c*)) from the femoral cortex, cutting through the cartilage and bone. Cutter 95 is impacted into femur 90 to form a first cut having an oval or oblong configuration (cross-section and perimeter).

FIGS. 3(*a*)-3(*c*) illustrate how the cutter 75 is distracted from the femur 90 with specific instrumentation (on the donor side), i.e., with a distractor assembly 80 comprising a handle 81 and a distractor 88. The cutter is distracted/removed from the femur by the following exemplary steps: remove impactor 72 and handle 71; assemble distractor 88 with a handle 81; thread distractor 88 into cutter 75; after the distractor 88 makes contact with the inserter 77, the inserter will be pushed to the cartilage surface; continuing to advance the distractor 88 will result in the cutter 75 backing out of the femur 90. FIG. 3(*c*) shows the cutter 75 and inserter 77 about completely removed from the femur 90 leaving femoral cut 91 having an oval or oblong cross-section.

FIGS. 3(*d*)-3(*f*) illustrate additional details and views of the threaded distractor 88 of the distractor assembly 80 of FIG. 3(*a*).

Figure 4A:
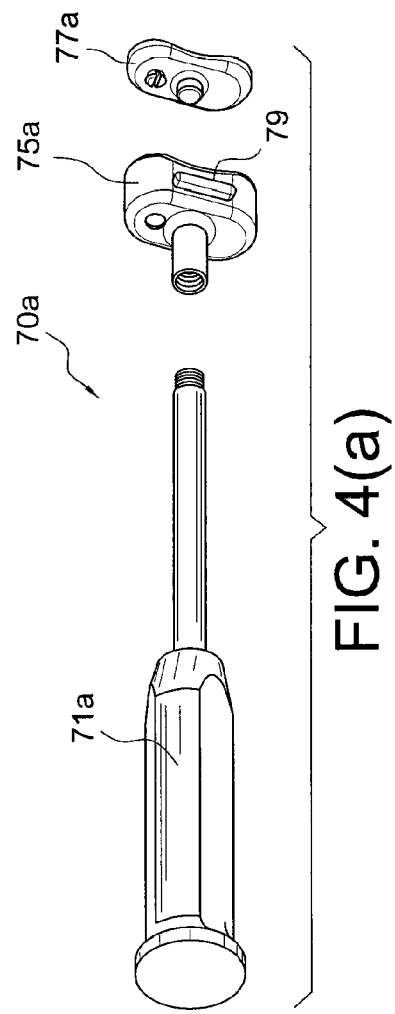
FIG. 4(a) illustrates an expanded view of an exemplary oblong depth guide system (used with a sagittal saw guide) of the present invention.
Figure 4B:
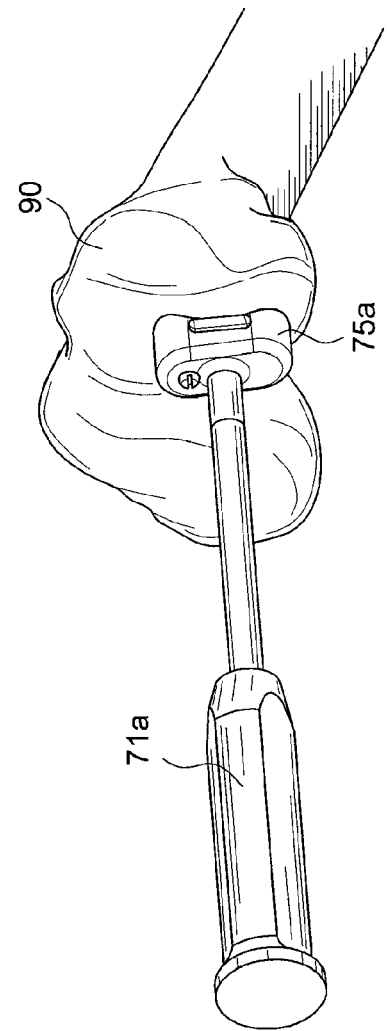
FIG. 4(b) illustrates cutting of the femur (to an exemplary 5 mm minimum depth) with the oblong depth guide system (used with a sagittal saw guide) of FIG. 4(a).
Figures 4C, 4E, 4F, 4G:
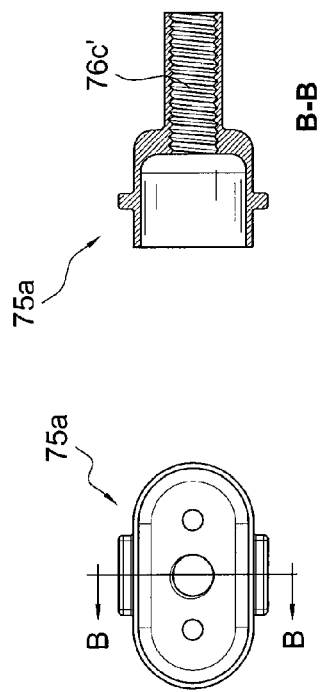

FIGS. 4(*a*) and 4(*b*) illustrate cutting femur 90 to a 5 mm minimum depth with oblong depth guide system 70*a* (second cutter assembly) and sagittal saw guide instrumentation (donor side). Oblong depth guide system 70*a* includes handle 71*a*, oblong depth guide 75*a* (second cutter) and insert 77*a*. Details of oblong depth guide 75*a* are illustrated in FIGS. 4(*c*)-4(*h*). Oblong depth guide 75*a* is about similar to the cutter 75 detailed above but differs in that the depth guide 75*a* is provided with slots 79 to allow a saw 85*a* to cut the femur to the desired depth, and as detailed below (i.e., in a second direction which is about perpendicular to the direction of the first cut). For example, depth guide 75*a* is also provided with a generally oval configuration as seen from the bottom view. Wall 76' has two curved portions 76*a*' adjacent and in contact with two straight portions 76*b*'. Wall 76' (that has a continuous oval perimeter) has a height "h" (FIG. 4(*d*)). Threaded cylindrical portion 76*c*' extends in a direction about parallel to that of the direction of wall 76'.

FIGS. 5(*a*)-5(*c*) illustrate depth cutting of the femur 90 by engaging guide 85 (third cutter) with depth guide 75*a* through arm 86 and by the following exemplary steps: insert oblong depth guide 75*a* to hard stop (the thin walled part will slip into the previously made cut); remove impactor handle; slip sagittal saw guide 85 over the oblong depth guide 75*a*; use a sagittal saw 85*a* (blade 85*a*) to cut the medial side of the donor femur 90; once again, use the distractor 88 (FIGS. 3(*a*)-3(*f*) to remove the oblong depth guide 75*a* against the inserter (because of the slip fit, this step may not be necessary); remove all instrumentation to reveal the implant 150 (FIG. 6). FIGS. 5(*d*)-5(*f*) illustrate additional details and views of the sagittal saw depth guide 85 of FIGS. 5(*a*)-5(*c*).

FIG. 6 illustrates donor implant 150 with a non-circular configuration (shape) of the present invention, having sidewalls 51 with an outer surface having a smooth configuration and defining a perimeter with a generally oblong and curved configuration (obtained by the first cuts formed with the cutter 75 and depth cutter 75*a*), a first surface 52 having a generally flat profile (obtained by the second cut formed with the sagittal saw blade 85*a*), and an opposing second surface 53 having the shape of the femoral cortex of the donor femur 90 (i.e., having a configuration that matches the surface contour and curvature of the defect region of a recipient femur). Donor implant 150 has a cross-section that is oval or oblong, or combination of oval and oblong, as viewed when taking a cut perpendicular to longitudinal axis 51*a*.

FIGS. 7(*a*)-11(*e*) illustrate the recipient side instrumentation for forming a recipient site to secure cut donor implant 150 (curved and oblong) therein. The recipient site (a femoral recipient site) is formed by methods of the present invention, as detailed below, and allows the as-formed recipient site to receive the exemplary donor implant 150 of FIG. 6.

Figure 7C:
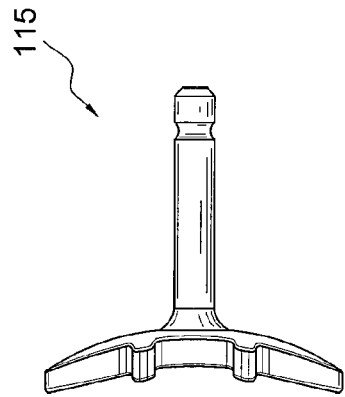
FIGS. 7(c)-7(f) illustrate additional details of the recipient guide of FIG. 7(a).
Figure 7D:
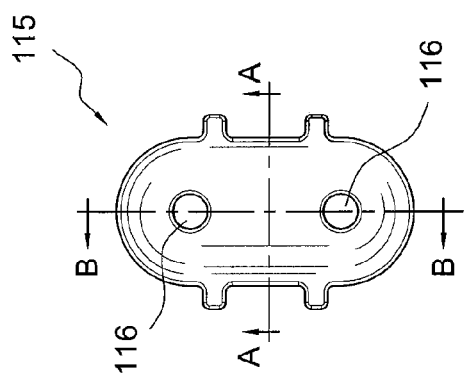
Figure 7F:
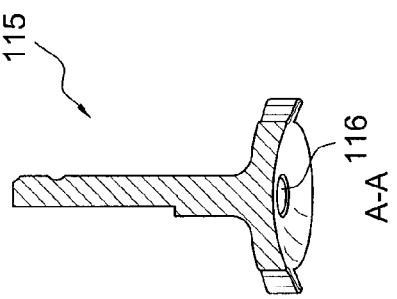
Figure 7E:
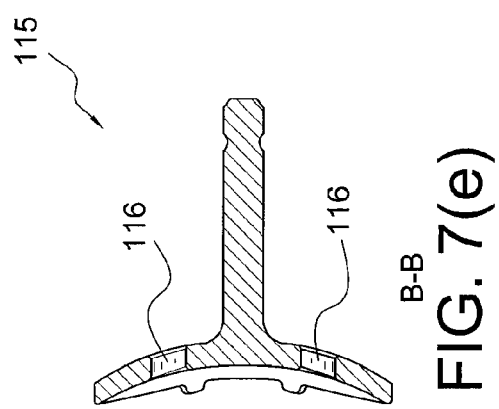
Figure 8:
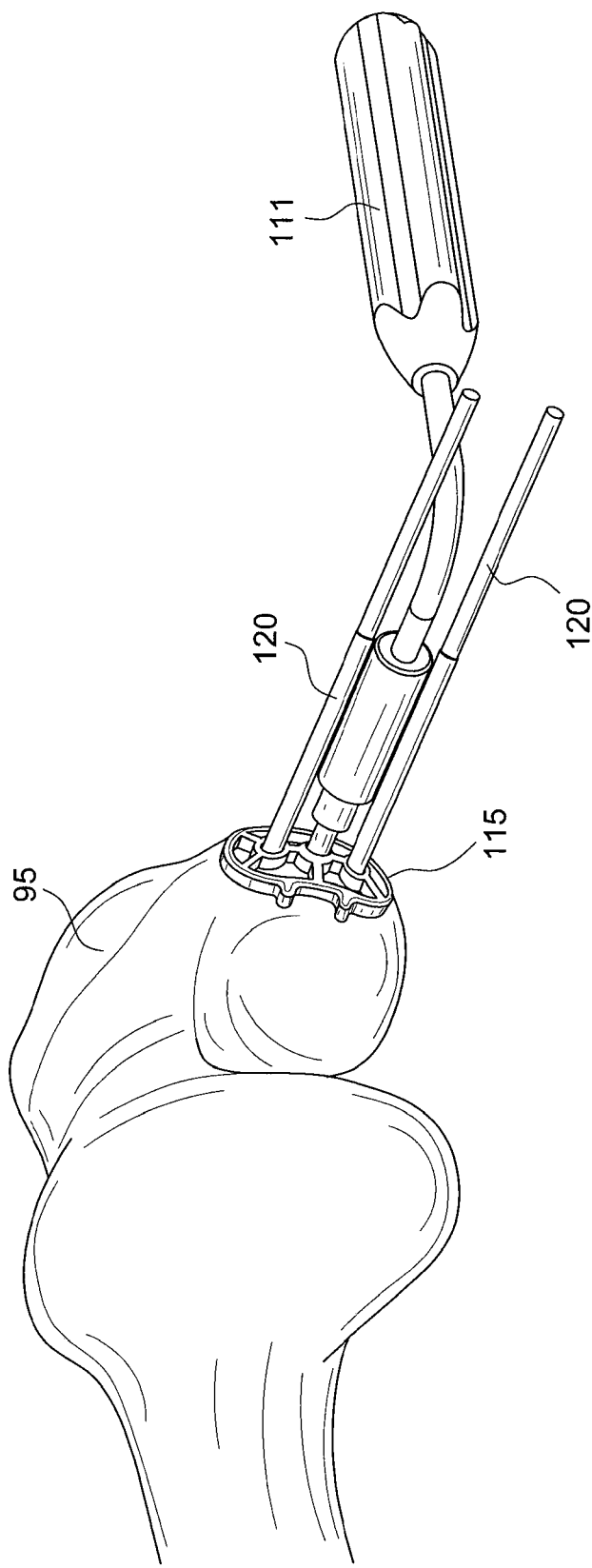
FIG. 8 illustrates the insertion of drill guide pins in the recipient guide of FIG. 17(a) (recipient side).

FIGS. 7(a) and 7(b) illustrate a recipient pin guide 110 used to match the curvature of recipient femur 95 (the femur on the recipient side). Recipient pin guide 110 comprises a handle 111 attached to a recipient guide 115. Details and additional views of the recipient guide 115 are shown in FIGS. 7(c)-7(f). Recipient guide 115 is provided with a body and two openings 116 to allow a plurality of drill guide pins 120 to pass therethrough. FIG. 8 illustrates the insertion of drill guide pins 120 (on the recipient side) with the recipient pin guide 110. The contour (perimeter) of the body of the recipient guide 115 resembles that of the outer perimeter of the donor implant 150.

FIGS. 9(a) and 9(b) illustrate the step of drilling the two ends of the oblong shape (that would define the shape of the recipient site in femur 95) with the two drills 120 (an anterior drilling procedure).

Figure 10F:
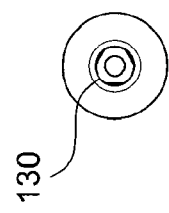
FIGS. 10(c)-10(g) illustrate details of the recipient drill (with cutting flutes) of FIG. 10(b).
Figure 10D:
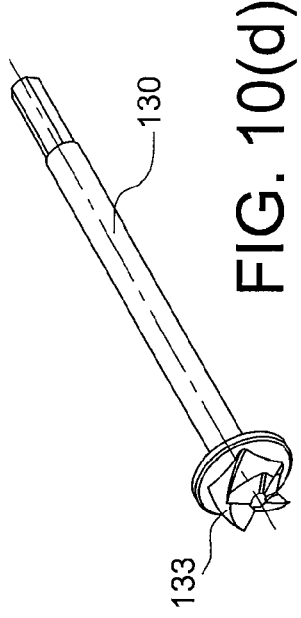
Figure 10C:
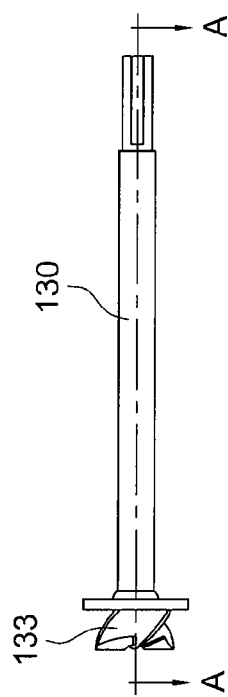
Figure 10G:
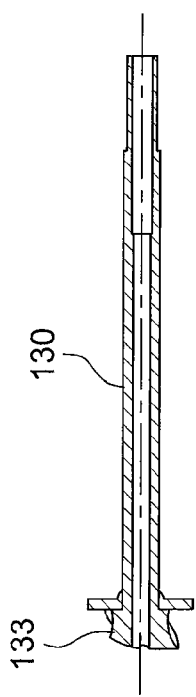
Figure 10E:
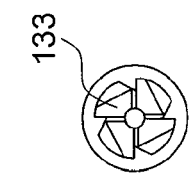

FIGS. 10(a) and 10(b) illustrate the step of drilling the ends of the oblong shape with the drills 120 (in a posterior drilling procedure—posterior drill). Recipient drill 130 with cutting flutes 133 is shown in more details in FIGS. 10(c)-10(g).

Figure 11A:
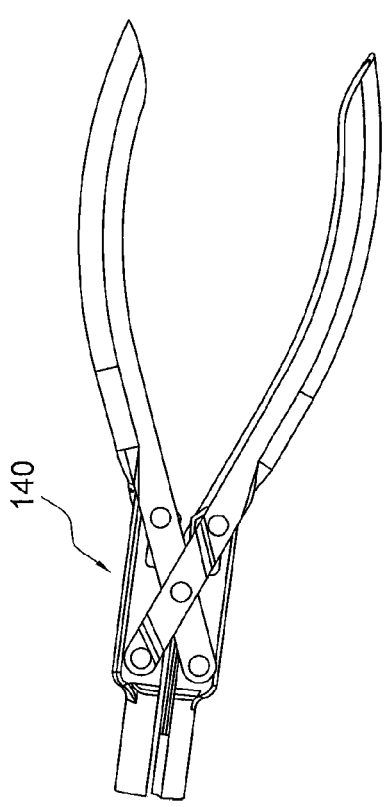
FIG. 11(a) illustrates a perspective view of an exemplary embodiment of cleaning pliers of the present invention.
Figure 11B:
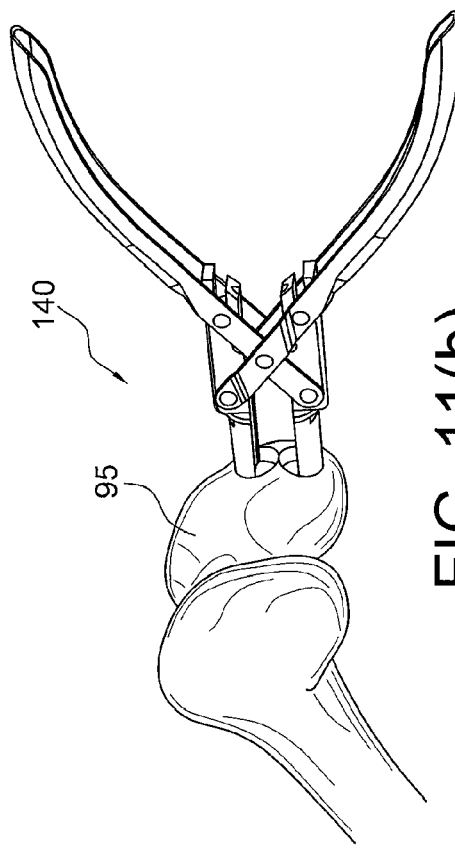
FIGS. 11(b) and 11(c) illustrate the pliers of FIG. 11(a) used to strip the sides of the oblong recipient hole formed with the instruments of FIGS. 9(a) and 9(b) and/or FIGS. 10(a) and 10(b).
Figure 11C:
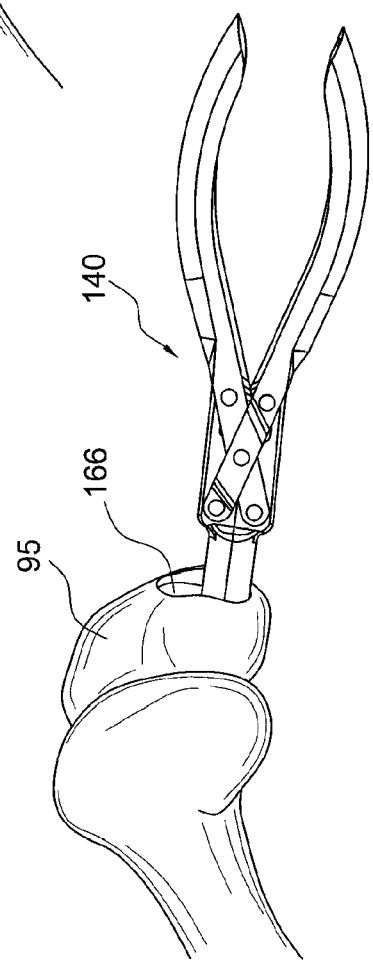
Figure 11E:
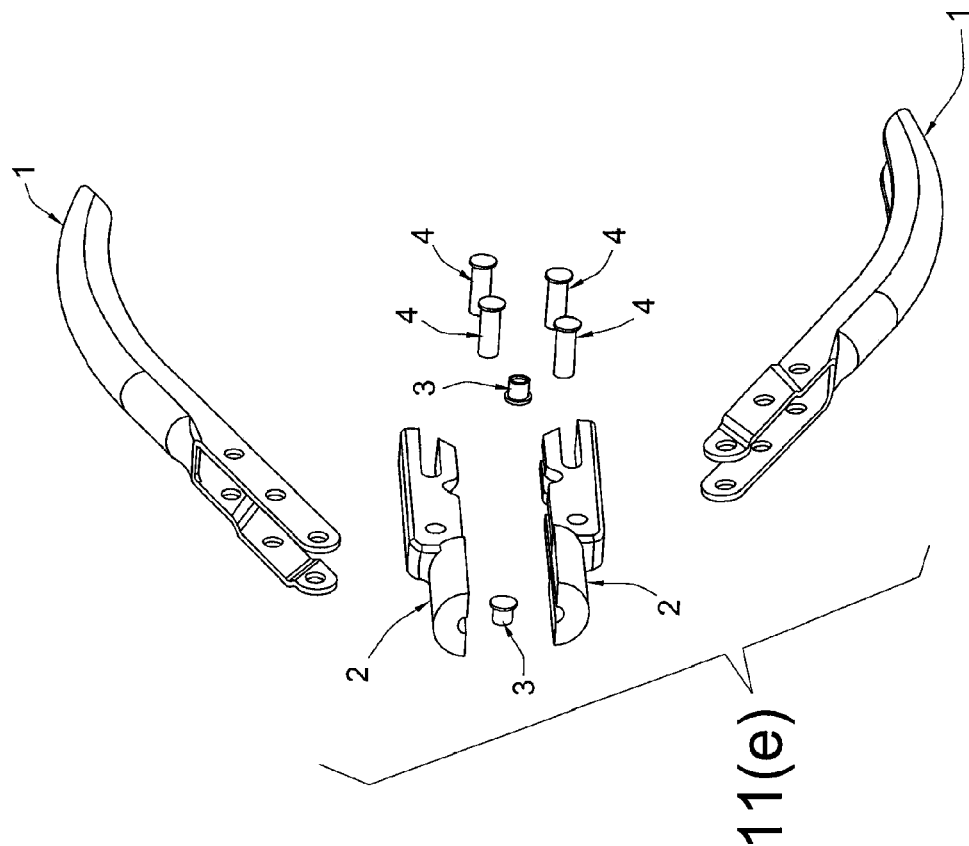
FIG. 11(e) illustrates an expanded view of the cleaning pliers of FIG. 11(d).
Figure 11D:
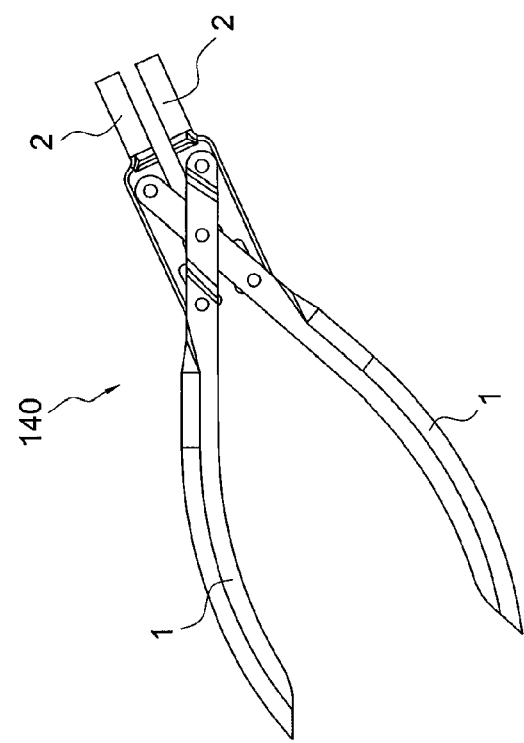
FIG. 11(d) illustrates another schematic view of the cleaning pliers of FIG. 11(a) (in the fully open position).

FIG. 11(a) illustrates an exemplary cleaning instrument 140 (cleaning pliers 140) of the present invention. The sides of the oblong hole are stripped (cleaned) with cleaning pliers 140 to form a recipient hole or through 166, as shown in FIGS. 11(b) and 11(c). Details and an exploded view of the cleaning pliers 140 are shown in FIGS. 11(d) and 11(e). The cleaning pliers 140 includes a plier handle 1, two anterior jaws 2, two short cross pins 3, and four long cross pins 4.

To assemble the instrument 140, the following steps may be followed: orient both items 1 as shown and insert both items 3 through the center hole of each side, such that the hollow end faces outward; pin hollow end of items 3 to secure it in place; slip 2 items 4 into the back holes in both items 1 (orient heads of long pins on same side of assembly); pin hollow end of items 4 to secure in place; slip 1 item 2 over lower item 4 and align with front hole in item 1; slip item 4 through items 1 and 2; pin hollow end of item 4 to secure it in place; repeat steps 5-7 for the upper item 4 to secure it in place; and lubricate and verify actuation of assembly.

FIGS. 12(a) and 12(b) illustrate the completion of the repair 100 of the present invention, by pressing the donor implant 150 into the recipient oblong hole 166 of recipient femur 95.

FIGS. 13(a)-18(b) illustrate another embodiment of the instrumentation of the present invention. FIGS. 13(a)-15(c) illustrate the donor side instrumentation for obtaining cut donor implant 150 (curved and oblong) of the present invention. FIGS. 16(a)-18(b) illustrate the recipient side instrumentation for forming a recipient site to secure cut donor implant 150 (curved and oblong) therein. The instruments of this embodiment differ, however, from the instruments of the first embodiment in slight changes both in the design and configuration of some of the instruments, and also in the sequence of steps employed.

FIGS. 13(a)-13(d) illustrate various elements of oblong cutter system 170 (first cutter assembly) that includes handle 171, impactor 172, oblong cutter 175, cutter insert 177 and guide pin 160. Oblong cutter 175 has a generally oval configuration as seen from the bottom view, for example (the configuration being about similar to that of the cutter 75 detailed above). System 170 is also provided with guide pin 160 that allows pin 161 to pass through a cannulation of the guide pin, as shown in FIG. 13(d), for example. Cutter insert 177 is also similar to the cutter insert 77 detailed above (i.e., configured to be received within the cutter 175).

FIG. 14(a) shows an enlarged view of exemplary distractor 188 (similar to distractor 88 detailed above) used to remove the cutter and insert of the system 170 of the present invention. Handle 82 (FIG. 14(b)) is attached to the distractor to remove the cutter insert 177 from the cutter 175 (FIG. 14(c)).

Figure 15A:
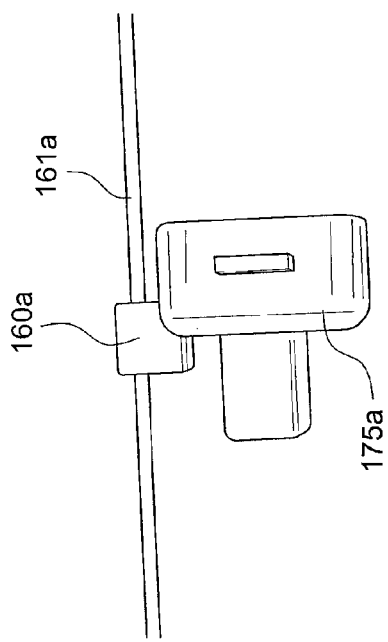
FIG. 15(a) illustrates an assembled view of an exemplary oblong donor depth guide (used with a sagittal saw guide) of the present invention.
Figure 15C:
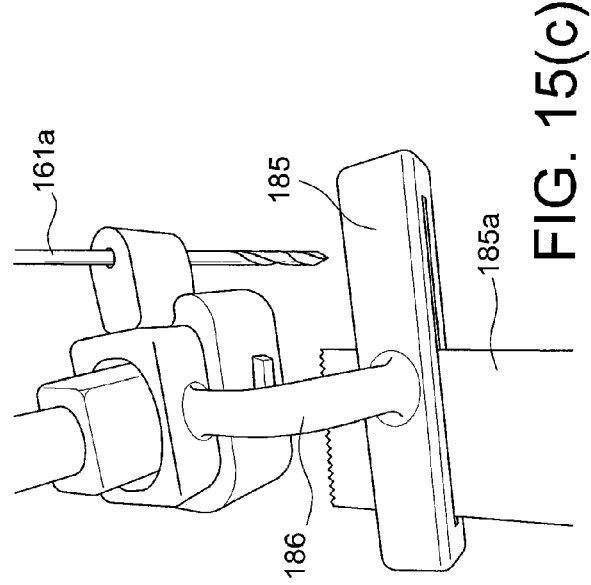
FIG. 15(c) illustrates the oblong donor depth guide assembled with the sagittal saw guide of FIG. 15(b), and further with an exemplary saw blade of the present invention.
Figure 15B:
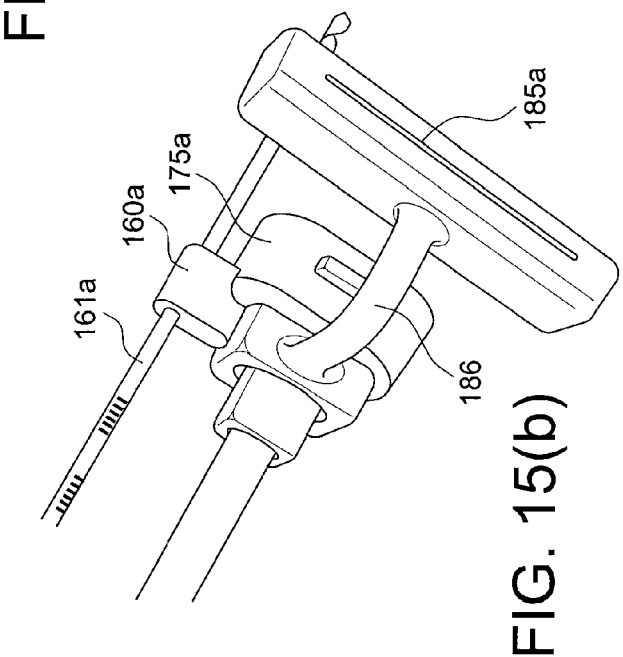
FIG. 15(b) illustrates an assembled view of the oblong donor depth guide of FIG. 15(a) assembled with a sagittal saw guide, and according to an embodiment of the present invention.

FIGS. 15(a)-15(c) illustrate an exemplary oblong donor depth guide 175a used with a sagittal saw guide 185 of the present invention. Saw blade 185a is employed with the saw guide 185 to cut the donor allograft cartilage and bone plug 150 by conducting a cutting motion in a direction about perpendicular to that formed by the oblong cutter 175, and as detailed above with reference to the second exemplary embodiment of the present invention.

Figure 16A:
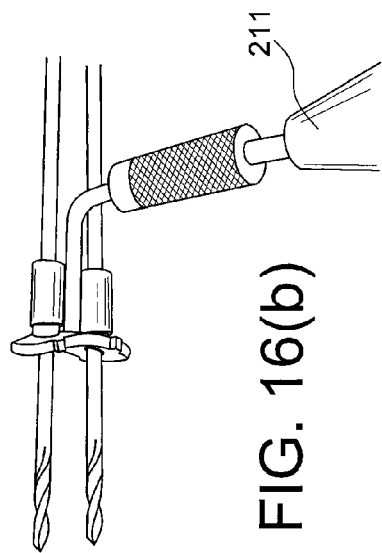
FIG. 16(a) illustrates a perspective view of an exemplary recipient sizing device and recipient drill guide of the present invention (used to match the curvature of the recipient femur (recipient side)), and according to yet another embodiment of the present invention.
Figure 16C:
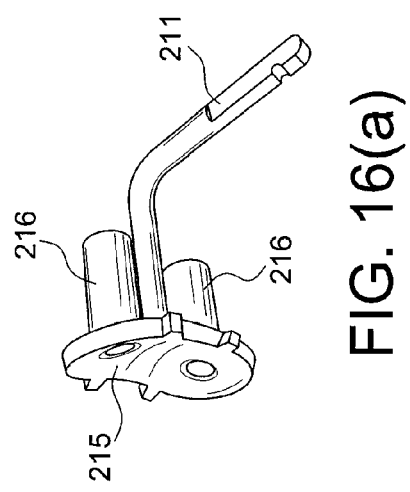
FIG. 16(c) shows another view of the assembly of FIG. 16(b).
Figure 16B:
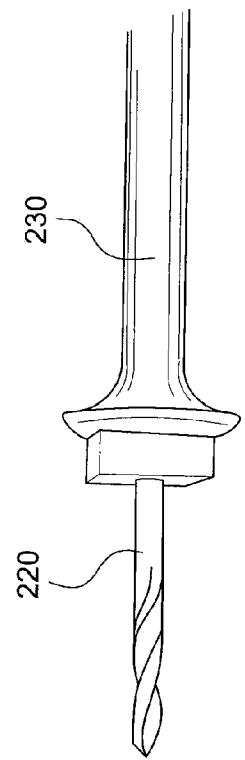
FIG. 16(b) illustrates the recipient sizing device and recipient drill guide of FIG. 16(a) also shown with a detachable handle and drill guide pins.
Figure 17:
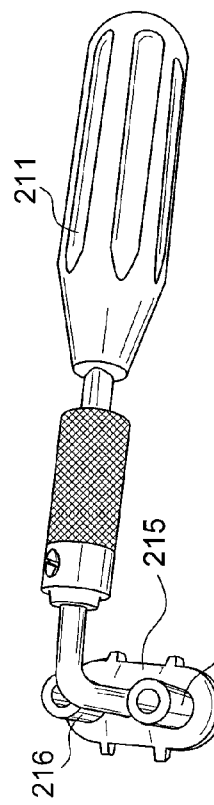
FIG. 17 illustrates a cannulated recipient drill shown with a drill guide pin and according to an exemplary embodiment of the present invention.

FIGS. 16(a)-18(b) illustrate instruments and systems on the recipient side, i.e., to form recipient site 166 of FIG. 22(a). FIGS. 16(a)-16(c) show sizing device 215 and recipient drill guide 216 (also shown with a detachable handle 211 and 4 mm drill guide pins). FIG. 17 shows a cannulated recipient drill 230 with an exemplary 4 mm guide pin 220.

Figure 18B:
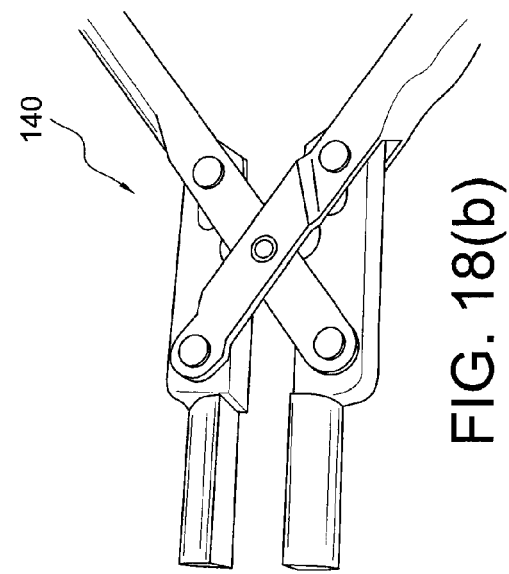
FIGS. 18(a) and 18(b) illustrate views of a recipient cleaning pliers (in the closed and open positions, respectively) and used on the recipient side of the present invention (used to strip the sides of the oblong recipient hole formed with the instruments of FIGS. 13(a)-15(c), for example.
Figure 17B:
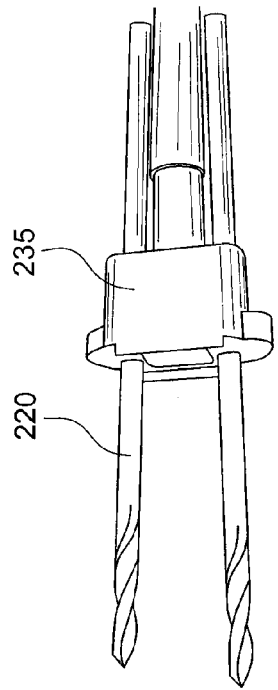
FIG. 17(b) illustrates the broach of FIG. 17(a) used with an impactor and slipped over exemplary 4 mm drill bits.
Figure 18A:
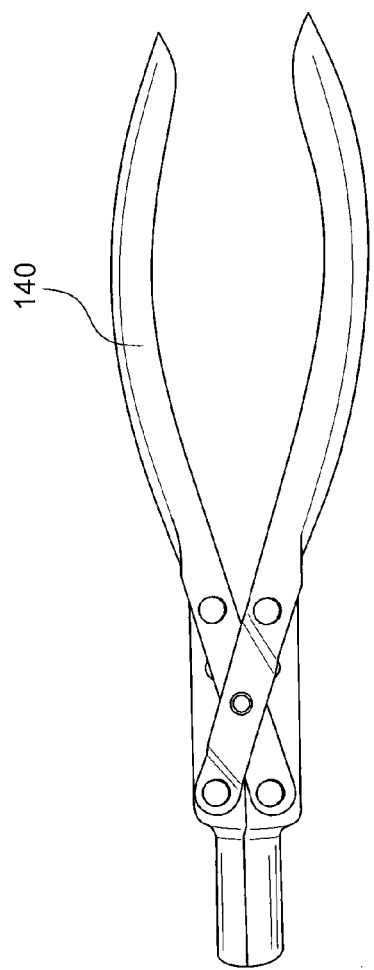
Figure 17A:
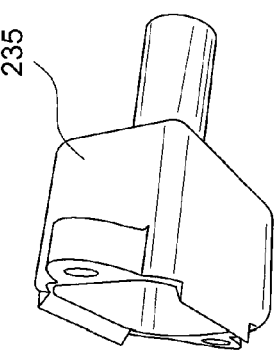
FIG. 17(a) shows an exemplary broach that can be used with the drill bits of the present invention.

FIGS. 17(a) and 17(b) show a broach 235 (also shown with impactor handle and slipped over 4 mm drill bits). FIGS. 18(a) and 18(b) show recipient cleaning pliers 140 which are similar to pliers 140 of FIGS. 11(a)-11(d). Cleaning pliers 140 are used to strip the sides of the oblong recipient hole 266 formed with the instruments of the present invention.

The present invention provides techniques and instruments for allograft femoral total knee reconstruction. A non-circular shaped allograft is extracted from a donor femur with specific instruments (and by specific methods) and then inserted into a recipient femur having a corresponding non-circular recipient site configuration. The methods of the present invention allow restoration of both the damaged cartilage and bone that occur in typical arthritic affections by providing completed allograft implants that are cut to a depth of about 5 mm minimum depth with specialized instruments (compared to current instruments that allow depth of only 6.35 mm at the narrowest portion regardless of the size of the femur).

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all falling within the scope of the invention.

What is claimed is:

1. A method of forming an allograft plug comprising cutting a donor femur in a first direction with a first cutter assembly; and
cutting the donor femur in a second direction with a second cutter assembly, the second direction being about perpendicular to the first direction,
wherein the allograft plug is a single piece and has a non-circular shape.

2. The method of claim 1, wherein the allograft plug comprises bone and cartilage.

3. The method of claim 1, wherein the allograft plug consists essentially of bone and cartilage.

4. The method of claim 1, wherein the non-circular shape is oval oblong.

5. The method of claim 1, wherein the first cutter assembly or the second cutter assembly comprises an oblong cutter.

6. The method of claim 1, wherein the first cutter assembly or the second cutter assembly comprises a cutter insert.

7. The method of claim 6, wherein the cutter insert has an outer shape and configuration that resembles a shape and configuration of an inner part of an oblong cutter.

8. The method of claim 6, wherein the cutter insert comprises a concave region.

9. The method of claim 1, wherein the first cutter assembly or the second cutter assembly comprises a guide pin.

10. The method of claim 9, wherein the guide pin allows a pin to pass through a cannulation.

11. The method of claim 1 further comprising depth cutting.

12. The method of claim 11, wherein the depth cutting comprises engaging the femur with a third cutter with a depth guide.

13. The method of claim 1, wherein the cutting the donor femur in the first direction or a second direction comprises cutting with a sagittal saw.

14. The method of claim 1, wherein the allograft plug comprises a surface contour and curvature of a defect region of a recipient femur.

* * * * *